United States Patent
Han et al.

(10) Patent No.: US 10,390,780 B2
(45) Date of Patent: Aug. 27, 2019

(54) METHOD AND X-RAY DEVICE FOR TEMPORAL UP-TO-DATE REPRESENTATION OF A MOVING SECTION OF A BODY, COMPUTER PROGRAM PRODUCT AND DATA CARRIER

(75) Inventors: Jing Feng Han, Shanghai (CN); Matthias John, Nürnberg (DE)

(73) Assignee: Siemens Healthcare GmbH, Erlangen (DE)

( * ) Notice: Subject to any disclaimer, the term of this patent is extended or adjusted under 35 U.S.C. 154(b) by 1257 days.

(21) Appl. No.: 13/554,435

(22) Filed: Jul. 20, 2012

(65) Prior Publication Data

US 2013/0023766 A1 Jan. 24, 2013

(30) Foreign Application Priority Data

Jul. 21, 2011 (DE) ........................ 10 2011 079 561

(51) Int. Cl.
*A61B 8/00* (2006.01)
*A61B 6/00* (2006.01)
(Continued)

(52) U.S. Cl.
CPC .............. *A61B 6/487* (2013.01); *A61B 6/504* (2013.01); *A61B 6/5235* (2013.01);
(Continued)

(58) Field of Classification Search
USPC ....................................................... 600/427
See application file for complete search history.

(56) References Cited

U.S. PATENT DOCUMENTS 8,099,155 B2 * 1/2012 Boese et al. .................. 600/427
8,494,245 B2 * 7/2013 Liao et al. ..................... 382/131
(Continued)

FOREIGN PATENT DOCUMENTS

CN 101243472 A 8/2008
CN 101252886 A 8/2008
(Continued)

OTHER PUBLICATIONS

Ameet Jain et al., 3D TEE Registration with X-Ray Fluoroscopy for Interventional Cardiac Applications FIMH 2009, LNCS 5528, Proceedings of the 5th International Conference of Functional Imaging and Modeling of the Heart pp. 321-329, 2009. Springer-Verlag Berlin Heidelberg 2009; Others; 2009.
(Continued)

*Primary Examiner* — Joel Lamprecht
(74) *Attorney, Agent, or Firm* — Lempia Summerfield Katz LLC

(57) ABSTRACT

A computer-implemented method for temporal up-to-date representation of a moving section of a body is provided. A first x-ray image data record is provided containing the moving section in a specific movement phase and a first 2D x-ray image and a 3D x-ray image superimposed and registered with one another. 2D x-ray images are repeatedly recorded each containing the moving section. 3D ultrasound images are repeatedly recorded each containing the moving section. Extended 2D x-ray images are created from the 2D x-ray images using the first x-ray images data record. The 3D ultrasound images are used as intermediaries for movement correction. The extended 2D images are displayed.

8 Claims, 1 Drawing Sheet

(51) Int. Cl.
*A61B 8/08* (2006.01)
*A61B 8/12* (2006.01)
*A61B 90/00* (2016.01)
*A61B 34/20* (2016.01)

(52) U.S. Cl.
CPC .......... *A61B 6/5247* (2013.01); *A61B 6/5264* (2013.01); *A61B 8/4254* (2013.01); *A61B 8/483* (2013.01); *A61B 8/5261* (2013.01); *A61B 6/4441* (2013.01); *A61B 6/488* (2013.01); *A61B 6/503* (2013.01); *A61B 8/0883* (2013.01); *A61B 8/0891* (2013.01); *A61B 8/12* (2013.01); *A61B 8/5276* (2013.01); *A61B 2034/2051* (2016.02); *A61B 2090/364* (2016.02); *A61B 2090/376* (2016.02); *A61B 2090/378* (2016.02)

(56) References Cited

U.S. PATENT DOCUMENTS

| | | | |
|---|---|---|---|
| 8,724,874 B2* | 5/2014 | Wein et al. | 382/131 |
| 9,036,880 B2* | 5/2015 | Hartung et al. | 382/131 |
| 9,058,664 B2* | 6/2015 | Liao et al. | |
| 2001/0029334 A1* | 10/2001 | Graumann | A61B 6/12 600/437 |
| 2007/0027390 A1 | 2/2007 | Maschke et al. | |
| 2008/0177172 A1* | 7/2008 | John et al. | 600/413 |
| 2008/0219540 A1 | 9/2008 | Ter | |
| 2009/0022383 A1 | 1/2009 | Falco | |
| 2009/0326373 A1* | 12/2009 | Boese et al. | 600/440 |
| 2010/0254583 A1 | 10/2010 | Chan | |
| 2011/0160589 A1 | 6/2011 | Fu | |
| 2011/0164035 A1 | 7/2011 | Liao | |
| 2011/0222750 A1* | 9/2011 | Liao et al. | 382/131 |
| 2013/0057569 A1* | 3/2013 | Liao et al. | 345/589 |
| 2013/0259341 A1* | 10/2013 | Mountney et al. | 382/131 |
| 2015/0015582 A1* | 1/2015 | Kaiser et al. | 345/427 |
| 2015/0223773 A1* | 8/2015 | John et al. | 600/424 |

FOREIGN PATENT DOCUMENTS

| | | |
|---|---|---|
| CN | 101903909 A | 12/2010 |
| DE | 102005032755 A1 | 2/2007 |
| DE | 102008030244 A1 | 12/2009 |

OTHER PUBLICATIONS

Pencilla Lang et al. Three-Dimensional Ultrasound Probe Pose Estimation from Single-Perspective X-Rays for Image-Guided Interventions Medical Imaging and Augmented Reality, Lecture Notes in Computer Science MIAR 2010. LNCS 6326, pp. 344-352, 2010; Magazine; 2010.

Razvan Ioan Ionasec et al., Robust Motion Estimation Using Trajectory Spectrum Learning: Application to Aortic and Mitral Valve Modeling from 4D TEE 2009 IEEE 12th International Conference on Computer Vision (ICCV), pp. 1601-1608; Others; 2009.

Namal Wijesinghe et al., A Novel Real-Time Image Processor to Facilitate Transcatheter Aortic Valve Implantation. The Paieon's C-THV System ACC 2010 Poster; Others; 2010.

Paieon C-THV—The Way to TAVI; Others; 2008.

German Office Action for German Application No. 102011079561.8, dated Jul. 5, 2018.

Chinese Office Action for Chinese Application No. 201210253272.3 dated Apr. 23, 2019, with English translation.

* cited by examiner

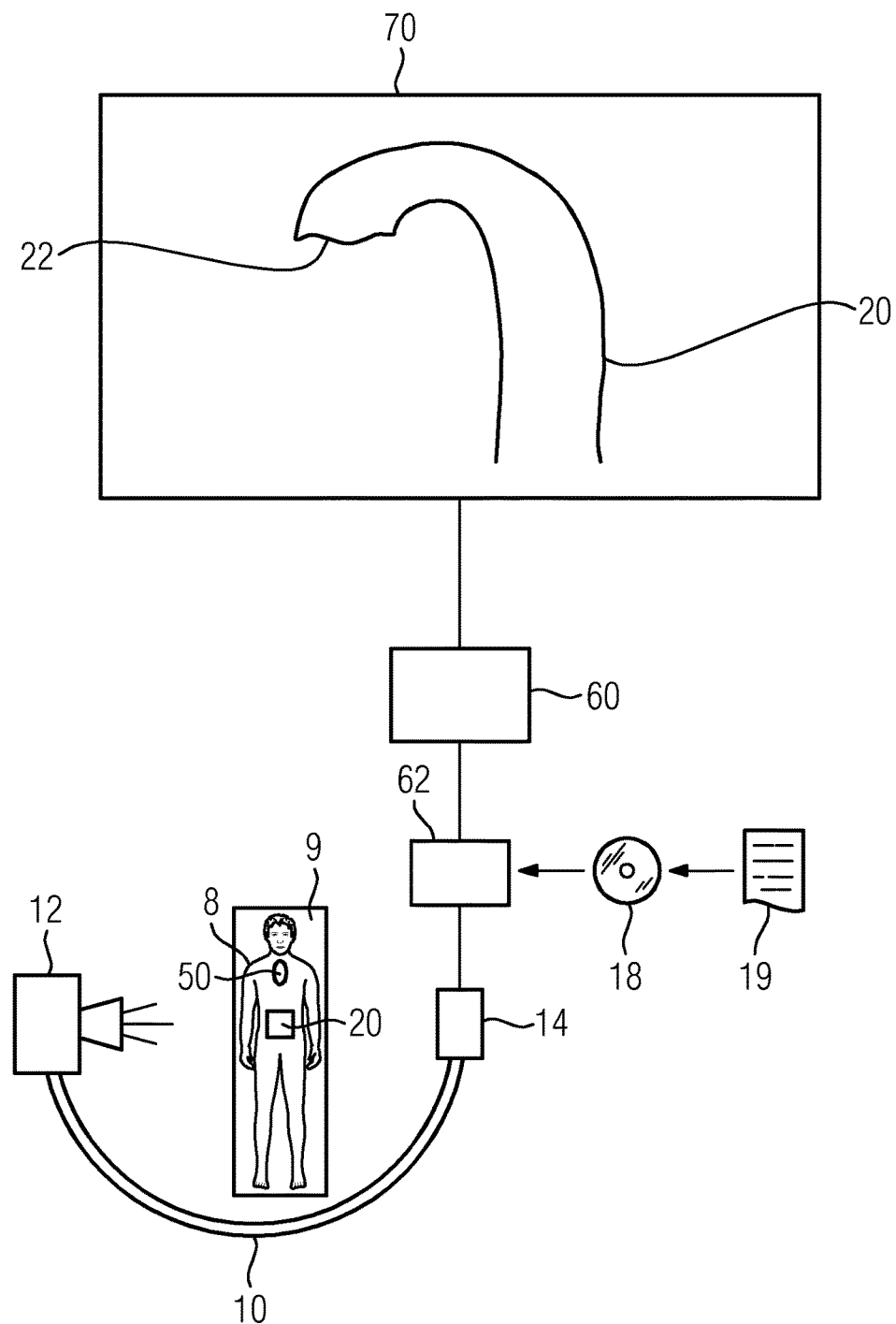

METHOD AND X-RAY DEVICE FOR TEMPORAL UP-TO-DATE REPRESENTATION OF A MOVING SECTION OF A BODY, COMPUTER PROGRAM PRODUCT AND DATA CARRIER

CROSS REFERENCE TO RELATED APPLICATIONS

This application claims priority of German application No. 10 2011 079 561.8 filed Jul. 21, 2011, which is incorporated by reference herein in its entirety.

FIELD OF INVENTION

The present application relates to a computer-implemented method and an x-ray device for temporal up-to-date representation of a moving section of a body. The application further relates to a computer program product, which implements the method, as well as a data carrier having a stored computer program product.

BACKGROUND OF INVENTION

Consistent attempts are made to improve medical imaging during interventions, wherein as few s as possible are simultaneously to be radiated onto the body of a patient. It is in many instances also very desirable to keep the stress on the body, such as on the kidneys, caused by the contrast agent which is required for x-ray recordings, to a minimum. One example to which this applies is the insertion of a new aortic valve. This example is subsequently used as an application area for the present application, without restricting the generality, wherein the application is naturally not restricted hereto.

Failure of the aortic valve, which is among the most frequent of valve faults, frequently results in damage and malfunction of the aortic valve. Contrary to the other valves within the heart, the aortic valve controls the flow of oxygen-rich blood, which is pumped out of the left ventricle into the aorta, which, as is generally known, is the main artery leading into the body.

The implantation of an aortic valve can be implemented as a minimally invasive heart operation, with which a faulty aortic valve is replaced by an artificial aortic valve. During the operation, real time fluoroscopy is frequently used by generating 2D x-ray images in order to provide navigation for the intervention. The problem nevertheless arises here of the aorta root barely being visible in the fluoroscopy images, if no contrast agent is injected. "Aorta root" is to be understood as the region of the aorta where it passes into and/or leaves the heart, in more precise terms, its left ventricle. Administration of (too much) contrast agent may however be problematic in many instances, because this may result for instance in renal insufficiency and injury to the patient. For this reason, it frequently occurs that a patient-specific aorta model, obtained by information extracted from an image, which is enriched with additional information, is merged with a fluoroscopy recording, i.e. superimposed and registered. In this way, a catheter can be localized in respect of the aortic valve and an optimal projection angulation for image representation can be determined for the subsequent implantation. The patient-specific aorta model is usually based on a segmentation of the aorta in preoperatively recorded CT volume data, of which a spatial recording by a C-arm device forms part.

If the patient-specific aorta model is overlaid with the fluoroscopy images, the physicians expect the model to move according to the heart and breathing movements of the patient, since an aorta model synchronized to the movement provides more accurate positioning information for the heart specialists during the replacement of the valve. A movement synchronization of this type is however currently only possible at the cost of a very high and thus possibly damaging contrast agent administration for the constant recording of a three-dimensional x-ray image.

DE 10 2008 030 244 A1 discloses a method for supporting percutaneous interventions, in which 2D x-ray recordings at different projection angles of an object range are recorded prior to the intervention using a C-arm x-ray system or a robot-based x-ray system and 3D image data of the object range is reconstructed from the 2D x-ray recordings. One or more 2D or 3D ultrasound images are recorded prior to and/or during the intervention using an external ultrasound system and are registered with the 3D image data. The 2D or 3D ultrasound images are then overlaid with the 3D image data record or a target area segmented therefrom or shown adjacent to one another in the same perspective.

SUMMARY OF INVENTION

The object underlying the present application is to specify a method and an x-ray device, a computer program product implementing the method and a data carrier storing the same, with which a permanent synchronization of a moving section in a body, for which the aorta and/or the aorta root was specified by way of example above, is enabled with the actual heart and breathing movement during medical interventions, such as transcatheter aortic valve implantations.

This object is achieved by a computer-implemented method for temporal up-to-date representation of a moving section of a body according to the independent claims. Developments of the application form the subject matter of the dependent claims.

In accordance with the application, a first x-ray image data record is initially provided, which contains the moving section in a specific moving phase, which can be arbitrary and is irrelevant to the application. This first x-ray image data record includes a first two-dimensional x-ray image in the form of a fluoroscopy image, also referred to as 2D x-ray image, as well as a three-dimensional x-ray image, also referred to as 3D x-ray image, which overlay one another and are registered with one another, which is also referred to as "merged". The "provision" of the first x-ray image data record means in many instances the recording of a 3D x-ray image and a 2D x-ray image and/or its derivation from the 3D x-ray image. The provision can however also take place such that a corresponding data record is retrieved from an archive. A patient-specific model of the moving section is extracted from the 3D x-ray image, e.g. by segmentation. The 3D x-ray image may be a previously obtained CT data record or a 3D image data record recorded using the C-arm device, on which the further method steps are also implemented. Alternatively, the model can also be determined from a 3D ultrasound image. The model can be very simple, e.g. a simple geometric figure or only one or a few points, which represent the position of an anatomical structure like the aorta root for instance.

In accordance with the application second 2D x-ray images are then subsequently repeatedly recorded, which naturally have to contain the moving section in each instance. The afore-cited x-ray images are recorded using a C-arm device. 3D ultrasound images are also repeatedly recorded, which similarly contain the moving section in each instance.

The idea underlying the disclosed solution of the afore-cited object is to use the 3D ultrasound images as an intermediary in each instance, in order to create third 2D x-ray images extended with additional information for instance from the second 2D x-ray images using the first x-ray image data record and then to indicate these. The recording of the 3D ultrasound images and the 2D x-ray images takes place at the same time and in real time, i.e. with a high temporal resolution. It is possible to update the position of the moving section in the 2D x-ray images in real time. This takes place by determining and updating the position of the afore-cited model of the moving section on the respective 3D ultrasound image, registering the 3D ultrasound image with the 2D x-ray image and then providing a superimposed representation of the updated model with the 2D x-ray image recorded in real time. In other words, the 3D ultrasound images are used to update and/or represent in real time the position of the moving section (from which it is assumed that it is clearly visible in the 3D ultrasound images but nevertheless scarcely visible or not visible at all in the 2D x-ray image) in the respective 2D x-ray image, without being assigned to a 3D x-ray image, such as is the case with the merged representation of the first x-ray image data record. In this way, moving sections in the 2D x-ray images can be shown in real time without being directly detectable by the 2D x-ray image recording. It is herewith possible in accordance with the application to be able to display all details of two different image acquisition and/or image creation systems in a single image in real time and/or without a temporal delay.

The ultrasound image generation is in many respects complementary to x-ray fluoroscopy. While ultrasound image generation provides a soft tissue contrast and a spatial representation, which enables easy visualization of complex heart anatomies and valve functions, catheters etc. are usually more clearly visible in fluoroscopy.

The disclosed method is also advantageous in that no new equipment for image acquisition or image preparation has to be installed in an operating room already equipped with various equipments, since the ultrasound image generation unit is generally already present and used in heart valve operations.

A further disclosure of the present application consists in the synchronization and/or movement components of the representation of the moving section taking place fully automatically in the 2D x-ray image.

In this application, the 3D ultrasound images are used to estimate the movement of the moving section, which is caused by heart and/or breathing activity and/or to detect the same by way of a model. The 3D ultrasound images, which are detected in real time, are used to update the position and/or model of the moving section, similarly in real time, in other words to adjust the same to the movement of the moving section. The updated model can be shown in real time supplemented with the 2D x-ray images. This takes place by a superimposed representation, in which for instance the updated model or a separate region of the moving section is projected onto the simultaneously recorded 2D x-ray image and shown transparently for instance.

According to a development of the application, an electromagnetic tracking method is used to determine the position and orientation of an ultrasound sensor used to create the ultrasound images. According to a development of the application, the 'live' recorded 3D ultrasound images can subsequently be registered and merged with the 2D x-ray images. An electromagnetic sensor is fastened to the ultrasound sensor or is integrated therein and a tracking sensor is fastened to a patient couch of an x-ray device used to record 2D or 3D x-ray images. It is clear that the two cited sensors can also already be provided prior to executing the disclosed method, for instance permanently, at the described positions. The 3D ultrasound images are then registered with the respective of the second 2D x-ray images by a transformation, wherein the transformation includes four subtransformations executed one after the other:

$$T(tee\_vol:x\_ray\_image)=T(tee\_vol:tee\_sensor)*T(tee\_sensor:em\_table)*T(em\_table:x\_ray\_vol)*T(x\_ray\_vol:x\_ray\_image),$$

wherein:
tee_vol are the ultrasound volume coordinates of 3D objects,
tee_sensor are the coordinates of the at least one ultrasound sensor,
em_table are the coordinates of the tracking sensor,
x_ray_vol are the volume coordinates of the 3D objects and
x_ray_image are the coordinates of the 3D objects in the respective of the 2D x-ray images.

A 3D x-ray image recorded using the C-arm device can herewith be used for calibration, since it detects the position of the ultrasound sensor relative to the C-arm device.

Alternatively to the afore-cited electromagnetic tracking method, the method described in the subsequent publication by Pencilla Lang et al. can also be used: "Three-Dimensional Ultrasound Probe Pose Estimation from Single-Perspective s for Image-Guided Interventions", Medical Imaging and Augmented Reality, Lecture Notes in Computer Science, 2010, Volume 6326/2010, pages 344 to 352.

The mode of operation of the disclosed method can be improved further if a segmentation is performed in order to mark a separate area in the 3D ultrasound images from the moving section, to which a particular position p(tee_vol) is assigned. This means in other words that the so-called "feature tracking" is applied to the 3D ultrasound images and as a result specific subregions or subsections can be better traced in the 2D x-ray images in respect of their movement. The particular position is then representative of the model or a part thereof and is used to determine the updated position of the model.

The feature tracking can be implemented for instance using techniques such as are described by Razvan Ioan Ionasec et al. in: "Robust Motion Estimation Using Trajectory Spectrum Learning: Application to Aortic and Mitral Valve Modeling from 4D TEE", International Conference on Computer Vision (ICCV), Kyoto, Japan, 2009, pages 1601 to 1608.

The particular position p(tee_vol) of the segmented moving section is transferred by a transformation T(tee_vol: x_ray_vol) into a segment position p(x_ray_vol) in the x-ray volume coordinates of the 3D objects and that the segment position p(x_ray_vol) be transformed by the transformation T(x_ray_vol:x_ray_image) into the correspondingly extended 2D x-ray image, as a result of which a movement correction of the overall moving section is enabled.

In a special application of the application to the implantation of a new aortic valve, a patient-specific model of the aorta is extracted from the moving section of the body by segmentation, wherein the aorta root is then selected as the separate area which receives an assigned special position.

When using transesophageol echocardiography (TEE) to obtain the 3D ultrasound images, very precise recordings can be achieved, since by positioning the ultrasound sensor in the esophagus, little interfering tissue is present between the ultrasound probe and the region to be observed which could interfere with the image recording. Concentration on the movement of the aorta root is also advantageous in that this is the region in which the aortic valve is to be inserted, wherein this can be shown the best and most precisely for the region of most interest to heart surgeons. Registration of the 3D ultrasound images with the 2D x-ray images takes place using techniques, such as (certainly only static and not dynamic, i.e. movement-compensated) are described by Ameet Jain et al. in: "3D TEE Registration with Fluoroscopy for Interventional Cardiac Applications", Proceedings of the 5th International Conference of Functional Imaging and Modeling of the Heart (FIMH), 2009, pages 321 to 329.

The present application is advantageous in that an electromagnetic tracking method can update the orientation and position of an ultrasound probe, such as a TEE probe, at any time in real time and fully automatically.

It also remains to be emphasized that when using the disclosed method, higher precision of the movement compensation can be achieved than for instance when tracing the head of a catheter. Applying the disclosed method ensures that position deviations of the represented areas from reality amount to 2 mm at most.

The solution of the object cited in the introduction is also achieved by a computer program product and/or a computer program, which can be used to control a control apparatus, which controls an image generation unit of an x-ray device, which executes the afore-cited disclosed method. A data carrier is also used to solve the object cited in the introduction, on which data carrier a corresponding computer program product is stored. The features described in respect of the disclosed method similarly also apply to the computer program product and the data carrier storing the same.

The object underlying the present application is also achieved with an x-ray device for temporally up-to-date representation of a moving section of a body, having: an x-ray emitter and an assigned x-ray detector, an x-ray image generation unit for generating a first x-ray image data record containing the moving section in a specific movement phase from the data recorded by the x-ray detector as well as for repeated generation of second 2D x-ray images, which each contain the moving section, an ultrasound image generation unit for repeated recording of 3D ultrasound images, which each contain the moving section, a control apparatus for controlling the image generation unit according to the afore-cited method and a display apparatus for displaying the extended 2D x-ray images.

Implementation of the afore-cited method in the control apparatus can take place in this way as software or also as (hard wired) hardware.

The embodiments of the disclosed method correspond to corresponding embodiments of the disclosed x-ray device. In order to avoid unnecessary repetitions, reference is made to the corresponding method features.

BRIEF DESCRIPTION OF THE DRAWINGS

Further features and details of the present application result from the subsequent description of the embodiments of the application. The single FIGURE shows a schematic representation of a disclosed x-ray device having a display apparatus and aorta displayed thereupon.

DETAILED DESCRIPTION OF INVENTION

The FIGURE shows a schematic representation of an x-ray device 10 embodied as a C-arm device, which includes an x-ray emitter 12 which can be pivoted in respect of the angular position and an x-ray detector 14 assigned and fixedly connected to the x-ray emitter 12. A patient 8 for diagnosis or therapy, such as for implantation of an aortic valve, can be arranged on a patient couch 9 between the x-ray emitter 12 and the x-ray detector 14.

The x-ray device 10 creates a required 3D x-ray image and "live" 2D x-ray images during an operation. Furthermore, a TEE probe 50 is shown in the esophagus of the patient 8, with which 3D ultrasound images can be generated during the operation, of the heart and/or aorta and/or its root.

A control apparatus 62, for instance in the form of a computer, is connected to the x-ray detector 14, said computer being connected to an x-ray image generation unit 60 for generating image data records from the data recorded by the x-ray detector 14. The image data supplied by the TEE probe 50 is likewise sent to the control apparatus 62, where it is used in accordance with the application in a manner described in more detail below.

The x-ray image generation unit 60 is in turn connected to a display apparatus 70 such as for instance a computer monitor, on which it can display the generated image data records. The x-ray image generation unit 60 can similarly be connected to a separate computer or microprocessor or however integrated in the control apparatus 62. The control apparatus 62 is controlled by a computer program 19, which can be stored for instance on a CD 18 as an example of a data carrier.

A variant of the disclosed method then proceeds as follows: the C-arm x-ray device 10 creates a 3D x-ray image of a region of interest, which the aorta root contains as a moving section 20 of a body 8 of a patient. Furthermore, the x-ray device 10 creates a 2D x-ray image, which contains the aorta root 20 and sends both x-ray images to the control apparatus 62. The two x-ray images are merged and/or registered with one another there and superimposed and processed to form a first x-ray image data record which is stored. Furthermore, the x-ray device 10 creates permanent 2D x-ray images, which contain the aorta root 20. Furthermore, the TEE probe 50 generates permanent 3D ultrasound images, which likewise contain the aorta root 20.

The method includes three main sections:
1) the registration of the "live" recorded 3-D-TEE-Bilder with the 2D x-ray images recorded by the C-arm device 10,
2) tracing the aorta root in the 3-D-TEE-images, and
3) updating the position of the aorta model in the 2D x-ray images.

Re (1): An electromagnetic tracking system is used to determine the position and the orientation of the TEE probe 50. The registration process proceeds as follows, wherein the following definitions apply:
  tee_vol are the ultrasound volume coordinates of 3D objects,
  tee_sensor are the coordinates of the at least one ultrasound sensor,
  em_table are the coordinates of the tracking sensor,
  x_ray_vol are the x-ray volume coordinates of the 3D objects and x_ray_image are the coordinates of the 3D objects in the respective 2D x-ray images.

1. The electromagnetic sensors are fastened to the TEE probe 50 or are integrated therein and a partial transformation between the TEE volume coordinates and the TEE probe 50 is provided by the calibration, which generally already takes place by the manufacturer. The assigned transformation reads as follows: T(tee_vol:tee_sensor).

2. An electromagnetic tracking sensor is fastened to the patient couch of the C-arm device 10 and to the TEE probe 50 (this process can naturally also already take place earlier). The transformation between the tracking sensor and the electromagnetic sensor on the TEE sensor 50 is embodied in real time by the electromagnetic tracking and takes place during or shortly after recording the 2D x-ray images. The assigned transformation reads: T(tee_sensor:em_table).

3. The transformation (already provided) between the 3D x-ray coordinates (i.e. in the physical world) and the patient couch is provided by the C-arm device 10. The assigned transformation reads: T(em_table:x_ray_vol).

4. Finally a transformation T(x_ray_vol:x_ray_image) is run which transforms 3D objects in their corresponding 2D positions in the 2D x-ray image.

The overall transformation between the 3-D-TEE-Volumen and the 2D x-ray image is finally given by: T(tee_vol:x_ray_image).

Re (2): During the operation, the cardiologists are above all interested in the precise position of the aorta root, where the stent and the flap are positioned. For this reason, the system performs a tracking of the aorta root in the 3-D-TEE-images and updates and/or determines the position of the aorta root in real time. This position is referred to using p(tee_vol). This process can be executed for instance using techniques which are described by Razvan Joan Ionasec et al. in "Robust Motion Estimation Using Trajectory Spectrum Learning: Application to Aortic and Mitral Valve Modeling from 4D TEE", International Conference on Computer Vision (ICCV), Kyoto, Japan, 2009, pages 1601 to 1608.

Re (3): The position p(tee_vol) of the aorta root, which was traced into the 3-D-TEE images is transformed by the transformation T(tee_vol:tee_sensor), T(tee_sensor:em_table) and T(em_table:x_ray_vol) into the position p(x_ray_vol) in coordinates of the C-arm system so that the position of the 3D image and/or a model determined therefrom, e.g. the aorta root can be corrected by using the observed movement. This position is then projected and/or transformed onto the 2D x-ray image by transformation T(x_ray_vol:x_ray_image).

It is ensured in this way that the registration between the 3-D-TEE-images and the 2-D-images take place in real time and fully automatically. An electromagnetic tracking method can update the orientation and position of the TEE probe at any time.

As already detailed, the tracking and/or tracing of the aorta root into the TEE images can provide a more precise three-dimensional movement of the aorta model for the valve implantation than for instance the tracking of the head of a catheter.

It is considered that the disclosed method and the disclosed x-ray device are closely linked to one another and that features of the application, which were described as method aspects, can also be essential to the x-ray device. Conversely, this can also apply to features described with reference to the x-ray device, which may also be relevant to the method.

It is also considered that with reference to individual embodiments, described features can also be realized in different embodiments, except when expressly described otherwise or precluded for technical reasons.

The invention claimed is:

1. A method for temporally up-to-date displaying a moving section of a body, comprising:
   providing an x-ray image data record comprising image data of the moving section in a movement phase, the image data record comprising a 2D x-ray image superimposed and registered with a 3D x-ray image, wherein the x-ray image data record is a patient-specific model of the moving section;
   segmenting the patient-specific model of the moving section in the 3D x-ray image;
   repeatedly recording 2D x-ray images comprising image data of the moving object in real time during a medical intervention using an x-ray device, wherein the x-ray device comprises an x-ray emitter, an assigned x-ray detector, and an x-ray image generation unit, or equivalents thereof, wherein the x-ray image generation unit comprises a computer, microprocessor, or equivalents thereof;
   repeatedly recording 3D ultrasound images comprising image data of the moving object in real time during the medical intervention using an ultrasound sensor, the 3D ultrasound images recorded simultaneously when recording the 2D x-ray images;
   determining and updating a position of the patient-specific model in real time using the recorded 3D ultrasound images and without assignment to a 3D x-ray image,
   registering the 3D ultrasound images with the simultaneously recorded 2D x-ray images in real time;
   creating real time 2D x-ray images from the recorded 2D x-ray images registered with the recorded 3D ultrasound images, the real time 2D x-ray images comprising the updated position of the moving section using the 3D ultrasound images, wherein the position of the moving section is projected onto the recorded 2D x-ray images in real time using the recorded 3D ultrasound images;
   superimposing the segmented patient-specific model of the moving section in the 3D x-ray image with the real time 2D x-ray images to show the updated position of the moving section in real time; and
   displaying the superimposed model of the moving section with a display device.

2. The method as claimed in claim 1, wherein a position and an orientation of the ultrasound sensor for recording the 3D ultrasound image is determined by an electromagnetic tracking method.

3. The method as claimed in claim 2, wherein an electromagnetic sensor is fastened on the ultrasound sensor or integrated therein and a tracking sensor is fastened to a patient couch of the x-ray device for recording the 2D x-ray image and/or the 3D x-ray image.

4. The method as claimed in claim 3, wherein the 3D ultrasound images are registered with the recorded 2D x-ray images by a transformation comprising:

$$T(\text{tee\_vol:x\_ray\_image}) = T(\text{tee\_vol:tee\_sensor}) * T(\text{tee\_sensor:em\_table}) * T(\text{em\_table:x\_ray\_vol}) * T(\text{x\_ray\_vol:x\_ray\_image}),$$

wherein:
tee_vol are the ultrasound volume coordinates of 3D objects, tee_sensor are the coordinates of the at least one ultrasound sensor,
em_table are the coordinates of the tracking sensor,
x_ray_vol are the volume coordinates of the 3D objects, and
x_ray_image are the coordinates of the 3D objects in the respective of the 2D x-ray image respectively.

5. The method as claimed in claim 1, wherein a separate region is characterized from the moving section by a segmentation of the 3D ultrasound image, and wherein the separate region is assigned a special position p(tee_vol).

6. The method as claimed in claim 5, wherein the special position p(tee_vol) is transferred into a segment position p(x_ray_vol) in x-ray volume coordinates of 3D objects by a transformation T(tee_vol:x_ray_vol), and wherein the segment position p(x_ray_vol) is transformed into the 2D x-ray images by a transformation T(x_ray_vol:x_ray_image) for correcting the position of the moving section.

7. The method as claimed in claim 1, wherein the 3D ultrasound image is recorded by transesophageal echocardiography, and wherein an aorta root is used as a separate region.

8. A device for temporally up-to-date displaying a moving section of a body, the device comprising:
an x-ray device comprising an x-ray emitter, an assigned x-ray detector, and an x-ray image generation unit, or equivalents thereof, wherein the x-ray image generation unit comprises a computer, microprocessor, or equivalents thereof, wherein the x-ray device is configured to record an x-ray image data record comprising image data of the moving section in a movement phase and to repeatedly record 2D x-ray images during a medical intervention, the 2D x-ray images comprising image data of the moving section in real time, wherein the x-ray image data record comprises an 2D x-ray image superimposed and registered with a 3D x-ray image;
an ultrasound image sensor configured to repeatedly record 3D ultrasound images comprising image date of the moving section in real time during the medical intervention simultaneously when recording the 2D x-ray images;
a computer that is configured to:
segment a patient-specific model of the moving section from the 3D x-ray image,
determine and update a position of the patient-specific model in real time using the recorded 3D ultrasound images and without assignment to a 3D x-ray image;
register the 3D ultrasound images with the simultaneously recorded 2D x-ray images in real time;
create real time 2D x-ray images from the recorded 2D x-ray images being registered with the 3D ultrasound images for updating the position of the moving section using the 3D ultrasound images, wherein the position of the moving section is corrected in real time by using the 3D ultrasound images; and
superimpose the patient-specific model of the moving section with the real time 2D x-ray images showing the updated position of the moving section in real time; and
a display device for displaying the superimposed model of the moving section.

* * * * *